United States Patent [19]

Lundbäck

[11] Patent Number: 5,722,404
[45] Date of Patent: Mar. 3, 1998

[54] SEALING ELEMENT FOR A BIOMEDICAL ELECTRODE

[75] Inventor: Stig Lundbäck, Vaxholm, Sweden

[73] Assignee: Humanteknik AB, Stockholm, Sweden

[21] Appl. No.: 693,239

[22] PCT Filed: Feb. 10, 1995

[86] PCT No.: PCT/SE95/00143

§ 371 Date: Aug. 9, 1996

§ 102(e) Date: Aug. 9, 1996

[87] PCT Pub. No.: WO95/21568

PCT Pub. Date: Aug. 17, 1995

[30] Foreign Application Priority Data

Feb. 11, 1994 [SE] Sweden ............................ 9400489
May 16, 1994 [SE] Sweden ............................ 9401673

[51] Int. Cl.$^6$ ........................................... A61B 5/0416
[52] U.S. Cl. ............................................ 128/643; 128/639
[58] Field of Search ................................ 128/643, 639, 128/640, 641, 644; 607/149, 152

[56] References Cited

U.S. PATENT DOCUMENTS

| | | | |
|---|---|---|---|
| 4,369,793 | 1/1983 | Staver et al. | 128/643 |
| 4,556,065 | 12/1985 | Hoffmann | 128/643 |
| 4,938,218 | 7/1990 | Goodman et al. | 128/643 |
| 5,345,935 | 9/1994 | Hirsch et al. | 128/643 |

FOREIGN PATENT DOCUMENTS

| | | |
|---|---|---|
| 0 289 905 | 11/1988 | European Pat. Off. |
| 27 35 041 | 2/1979 | Germany |
| 35 01 339 | 7/1986 | Germany |
| 454 941 | 6/1988 | Sweden |
| 992021 | 1/1983 | U.S.S.R. |
| 93/16633 | 9/1993 | WIPO |

Primary Examiner—John P. Lacyk
Assistant Examiner—David Ruddy
Attorney, Agent, or Firm—Hill, Steadman & Simpson

[57] ABSTRACT

A biomedical vacuum electrode, such as an ECG electrode, is provided with a sealing element which improves performance. The sealing element includes a body and a sealing lip which extends around the body and terminates in a sealing edge at an application side. An inner surface of the sealing lip defines a vacuum chamber adapted in use of the electrode to communicate with a source of vacuum through a vacuum passageway. The vacuum passageway is connected with the vacuum chamber at the inner side of the sealing lip adjacent the sealing edge and opens into the vacuum chamber by way of an annular opening or gap. A contaminant absorber is placed on the side of the sealing element body facing away from the sealing edge to absorb contaminants carried away from the region of the sealing edge through the passageway.

20 Claims, 3 Drawing Sheets

SEALING ELEMENT FOR A BIOMEDICAL ELECTRODE

BACKGROUND OF THE INVENTION

This invention relates to biomedical electrodes, namely suction or vacuum electrodes for use in carrying out examinations or treatments in which an electrode element is kept in electrical contact with the skin of a patient. Examples of such electrodes are ECG and EEG electrodes. More particularly, the invention concerns a sealing element for a biomedical electrode, namely a sealing element having an annular sealing rim or lip which terminates in a sealing edge adapted to engage the skin. The sealing element forms a vacuum bell or cup defining a vacuum chamber in which the electrode element is positioned.

In use of the vacuum electrode, the sealing element is attached to an electrode holder having a vacuum port connected to a source of vacuum. An air passageway provides communication between the vacuum chamber and the vacuum port. When the sealing edge of the sealing lip engages the skin of the patient and the thus sealed vacuum chamber communicates with the vacuum port, the ambient air pressure can press the electrode element in the vacuum chamber against the skin of the patient through the intermediary of the electrode holder.

An example of a known sealing element of the general kind with which the present invention is concerned is disclosed in WO93/16633.

In use of electrodes of the kind mentioned above, wet contaminants in the form of sweat or other secretions from the skin area to which the electrode is applied are often present. In many cases, conductive gel, saline or other conductive agents are applied to the skin to improve electrical contact between the skin and the electrode element.

It has been found that the contaminants—unless otherwise specified, the term "contaminants" as used hereinafter includes perspiration conductive gel, saline and the like— often have an unfavourable and unpredictable influence on the signals picked up from the patient through the electrode element, for example in ECG measurements.

An explanation for this unfavourable influence is not yet fully verified. However, one contributory cause is believed to be that because of the conductive contaminants, the electrode element is in electrical contact with the skin not only over the specific defined skin area which is engaged by the electrode element, but also over an indeterminate surrounding skin area.

A further contributory cause may be that the electrical contact of the electrode element with the skin varies during the course of the examination or treatment.

An unavoidable leakage of air between the skin and the circumferential sealing edge of the sealing element and air bubbles which enter the vacuum chamber and migrate along the skin around the electrode element are believed to be another cause for the variations. A further possible cause is a gradual drying up of the contaminants during use of the electrode.

The variations result both in variations of the conductivity of the interface region between the electrode element and the skin and, when static electric fields are present, in dipole variations on and beneath the surface of the skin, and consequent strong spurious signals.

Until now, the disturbing effect of the static fields on the signal quality of vacuum electrodes has not been clearly identified. Instead, the disturbances that have occurred, have been attributed to conductivity variations.

SUMMARY OF THE INVENTION

The primary object of the invention is to provide a solution to the problem described above, namely to provide a vacuum electrode in which the electrical connection between the electrode element and the skin area to which the vacuum electrode is applied is not subject to variations of the kind explained above.

To this end, the invention provides a vacuum electrode device and a sealing element for a vacuum electrode device. The sealing element includes a vacuum cup defining a vacuum chamber adapted to accommodate a skin-engaging portion of an electrode element and communicating with a vacuum passageway through which a vacuum can be applied to the vacuum chamber. The vacuum cup has a skin-engageable outer sealing edge disposed around an opening to the vacuum chamber. The sealing element also includes means for conducting fluid away towards the vacuum passageway from a narrow annular zone or gap inwardly adjacent to the outer sealing edge. The gap is delimited outwardly by the outer sealing edge.

In an embodiment, the vacuum cup further includes an annular outer sealing lip which has an annular free end forming an outer sealing edge, the outer sealing lip defining together with the body the vacuum chamber, and the vacuum cup also includes a generally disk-shaped body is concentrically positioned within the vacuum chamber. The body has an annular inner sealing lip which includes a skin-engageable inner sealing edge spaced from the outer sealing edge to form the narrow annular gap. This body subdivides the vacuum chamber into a central inner vacuum chamber compartment and an outer annular vacuum chamber compartment into which the vacuum passageway opens.

In an embodiment, the inner sealing edge is spaced radially inwardly from the outer sealing lip and lies in a generally common plane therewith.

According to an embodiment, the inner sealing lip is flexible.

Also, in an embodiment, the body extends generally transversely from a central axis of the sealing element, and a peripheral portion of the body carries the inner sealing lip which is positioned at the vacuum passageway.

In a another embodiment, the body has a central recess for accommodating a skin-engaging portion of an electrode element and wherein the body has an annular skin-engaging rib disposed concentrically around the recess and concentrically inwardly of the inner sealing lip. The rib is adapted to project into the inner vacuum chamber compartment slightly past the skin-engaging portion of the electrode member.

Preferably, a moisture absorber is disposed within the fluid flow path through the outer vacuum chamber compartment. In a related embodiment, the moisture absorber extends into the outer vacuum chamber compartment.

The means for conducting fluid towards the vacuum passageway, in an embodiment, may include capillary passages in the outer sealing lip. Also, the means for conducting fluid towards the vacuum passageway may include a moisture absorber element in the annular gap.

Another aspect of the invention is to provide a vacuum electrode device having an electrode head with means for connecting it to a vacuum pressure source and to an apparatus for processing electric signals. Such a vacuum electrode device includes a sealing element according to the aforementioned description.

Basically, the solution according to the invention consists in carrying away the contaminants from a zone surrounding the area of the skin in which variations in the electrical connection between the skin and the electrode element are to be avoided, in a manner such that the electrical environment sensed by the electrode element is affected as little as possible.

Additional features and advantages of the present invention are described in, and will be apparent from, the detailed description of the preferred embodiments and from the drawings.

DETAILED DESCRIPTION OF THE PREFERRED EMBODIMENTS

Figure 1:
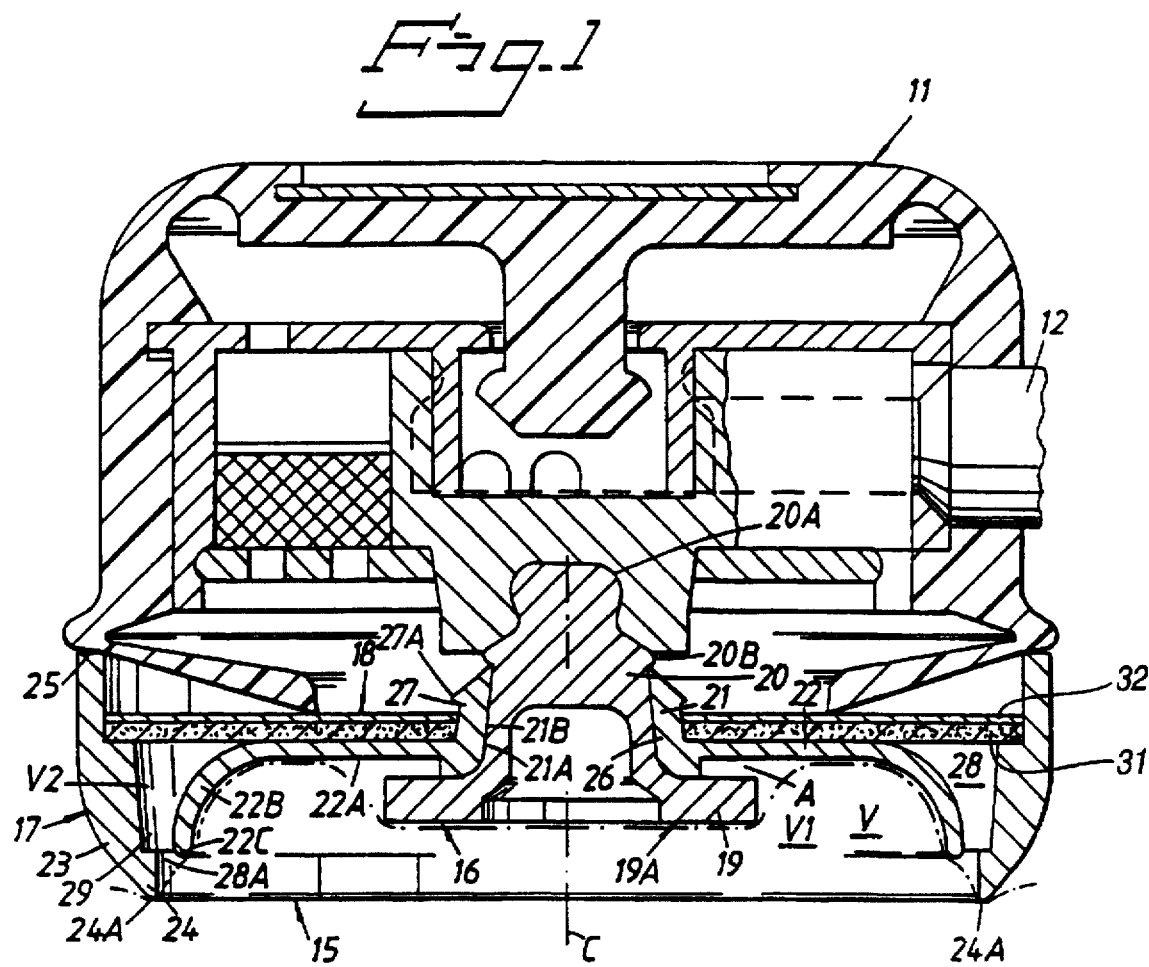
FIG. 1 is a central vertical sectional view of a vacuum electrode device incorporating a sealing element according to the invention.

The vacuum electrode device shown in FIG. 1 is intended for use in ECG measurements and comprises two main parts. One of these main parts is an electrode holder or head, generally designated by 11, which is adapted to be connected through a wire and hose assembly 12 to an ECG apparatus (not shown) which comprises a vacuum and pressure pump and circuitry for processing and recording electric signals taken up by means of the electrode device. The other main part is an electrode unit, generally designated by 15, which is attached to the electrode holder in a manner that permits it to be readily detached from it.

Electrode holder 11 is constructed substantially as illustrated and described in WO93/16633 (FIGS. 7–9). As the detailed construction of the electrode holder 11 does not form part of the present invention, it will not be described in detail here. Instead, for a detailed description of the construction and operation of the electrode holder 11, reference is made to the just-mentioned publication, which is incorporated in the present disclosure by reference.

In the embodiment illustrated in the drawings, the electrode unit 15 is made up of three parts which are detachably interconnected: an electrode element 16, a sealing element 17 and a contaminant absorber 18. The contaminant absorber 18 and the sealing element 17, which serves as a support or mount for the contaminant absorber 18, form an independent subunit or subassembly (shown in FIG. 2) of the electrode unit.

Electrode element 16, which is circular in plan view and has a central axis C may be made of plastic and provided with an electrically conductive surface coating. It comprises a lower portion forming a disc-shaped skin engaging or contacting member 19 the underside 19A of which is adapted in use of the electrode device to engage the skin of a patient, and a shank 20 which extends upwardly from the upper side of the skin engaging portion and includes a contact head 20A by means of which the electrode element 16 and, consequently, the entire electrode unit 15 is releasably attached to the electrode holder 11.

Sealing element 17 is integrally made from a polymer material, for example, or from some other suitable nonconducting material and comprises: a centre or hub portion 21 which forms a socket or recess 21A for the electrode element 16 and is slid over the shank 20 thereof, a circular body 22 having a flat upper side and extending transversely of the axis C of the hub portion, and an annular sealing rim or lip 23 which extends around the periphery of the body 22 to define a vacuum compartment V between the electrode holder 11 and the skin of the patient. The sealing element 17, which thus forms an inverted suction or vacuum cup having a vacuum chamber defined by the underside of the body 22 and the sealing lip 23, is adapted to engage the skin of the patient by its annular lower sealing edge 24 and to engage the underside of the electrode holder 11 by its annular upper edge 25. The body 22 forms a seat which receives the contaminant absorber 18 and holds it in position on the sealing element.

Suitably, the sealing element 17 is sufficiently rigid to permit of manipulation thereof by means of production and assembling apparatus. On the other hand, it should have some elasticity, at least in the region of the sealing edge 24, such that this region can be flexed inwardly to some extent when the sealing element is pressed against the skin to thereby make the lowermost portion of the sealing lip "undercut".

A tubular collar 26 on the hub portion 21 extends downwardly from the sealing element body 22, and its lower edge engages the upper side of the skin engaging member 19 of the electrode element 16 such that an air gap A exists between the underside of the body 22 and the upper side of the outer portion of the skin engaging member 19 which projects laterally beyond the hub portion 21. Suitably, the height of this air gap A may be about 1 mm.

Moreover, the hub portion 21 comprises a tubular neck 27 which extends upwardly from the body 22 and the upper end of which is positioned immediately below a small annular bead 20B on the shank 20 of the electrode element 16. Accordingly, there is a snap-type attachment of the electrode element 16 to the sealing element 17 such that these two parts of the electrode unit 15 can readily be interconnected and separated and, when interconnected, are reliably held together in a well-defined position relative to one another as shown in FIG. 1.

At the upper end of the neck 17 on the hub portion 21 of the sealing element 17 a small external annular bead 27A is provided which ensures a snap-action attachment of the contaminant absorber 18 to the sealing element 17.

Figure 2:
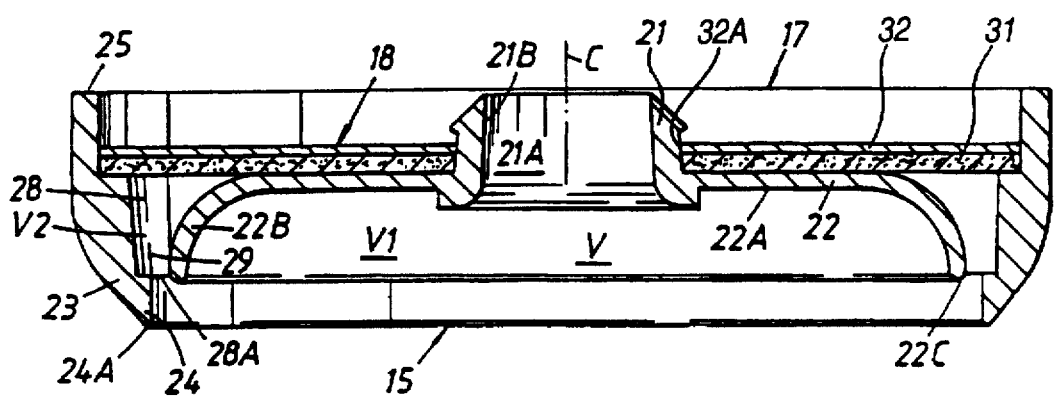
FIG. 2 is a sectional view, taken on line II—II in FIG. 3 of a unit which forms part of the electrode device of FIG. 1 and comprises a sealing element and a contaminant absorber supported by the sealing element.
Figure 3:
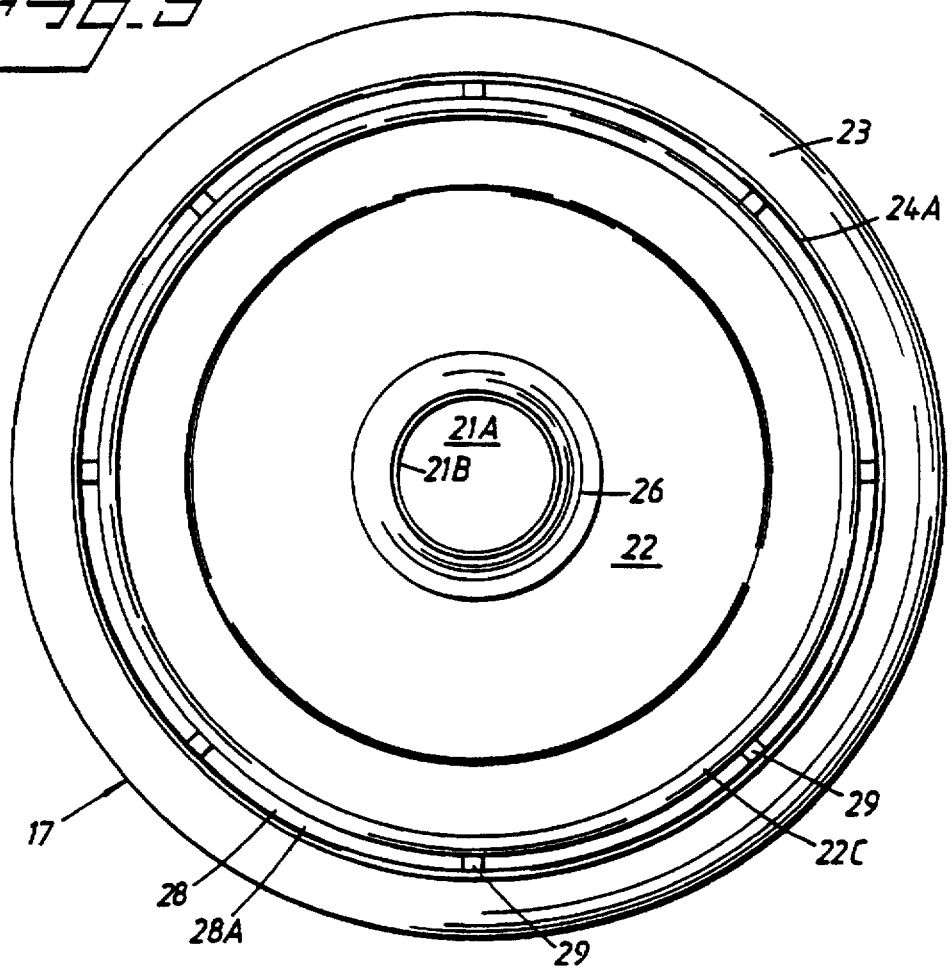
FIG. 3 is a base view of the unit shown in FIG. 2.

In the illustrated exemplary embodiment the underside 22A of the sealing element body 22 is generally flat from the hub portion 21 over the major portion of the distance up to the sealing lip 23, but its radially outer portion is curved downwardly as shown in FIGS. 1 and 2. Together with the inner side of the sealing edge 24 of the sealing lip 23, the radially outer, downwardly curved portion 22B of body 22 forms a circumferential passageway 28 including an opening in the form of a narrow gap 28A extending throughout the circumference of the sealing lip. The body portion 22B is connected with the sealing lip 23 through a number of circumferentially spaced, narrow and short webs 29.

The lower outer edge 22C of the body portion 22B extends downwardly a short distance beyond the webs 29 and is situated slightly higher than the narrow rounded tip 24A of the sealing edge 24; the difference in level between the edge 22C and the tip 24A may be, for example, about 1 millimeter in an ECG electrode.

The just-mentioned gap 28A constitutes the main or sole fluid flow path between the upper and lower portions of the vacuum chamber V which lie on opposite sides of the sealing element body 22. Apart from the recess 21A and the passageway 28, the body 22 is imperforate, and although no separate seal is provided between the electrode element 16 and the hub portion 21 of the sealing element, no significant fluid flow occurs between these elements.

As is apparent from FIGS. 1 and 2, the body portion 22B subdivides the vaccum chamber V into an inner or central compartment V1 and an annular outer compartment V2 which communicates with the inner compartment through the annular gap 28A.

It is important in use of the electrode device that sweat and other fluid or wet contaminants are prevented from forming an unstable conducting path between, on the one hand, the skin area surrounding the sealing element 17 and, on the other hand, the electrode element 16. When an exercise ECG is taken, the patient often perspires heavily so that his skin often becomes covered with sweat both around the electrode device and under it. The patient's movements inevitably result in some leakage of air and resulting migration of sweat along the skin under the sealing edge 24. Even when the patient does not move, such leakage of air and migration of sweat can also take place through narrow capillary passageways at hairs which extend along the skin across the sealing edge.

In accordance with the invention, however, because of the location or arrangement of the narrow opening gap 28A of the vacuum passageway 28 relative to the vacuum chamber V, any air leaking into the vacuum chamber V in use of the electrode will be immediately carried away from the skin upwardly along the inner side of the sealing edge 24 and through the passageway 28 to the absorber 18. The interface through which an electrical connection between the skin and the electrode element 16 can be established will therefore be restricted essentially to the well-defined area which is delimited by the edge 22C and in any case will not extend beyond the sealing edge 24. Moreover, no fluid movement along the interface between the skin and the underside of the sealing element body 22 will occur, and the fluid movement that occurs within the sealing element will take place at the peripheral portion and will be directed generally axially (the webs 29 contribute to restricting circumferential flow).

Contaminant absorber 18 is positioned on the upper side of the body 22 of the sealing element 17. In the illustrated embodiment the contaminant absorber comprises a circular disk 31 of a material with high capability of absorbing and retaining moisture, preferably a so-called superabsorbent material, and a cover disk 32 which is substantially congruent with the absorber disk and impermeable at least to moisture (some permeability to air can be accepted). In the illustrated embodiment the cover disk 32 is a separate thin disk of plastic, waxed paper or the like which covers the absorber disk 31, but it my also be integrated with the absorber disk 31 and produced by spreading or otherwise applying a sealing composition on the absorber disk, for example. Air can readily flow from passage 28 around the periphery of the contaminant absorber 18 into the portion of the vacuum chamber V which is formed above the contaminant absorber.

The position of the contaminant absorber 18 over the vacuum passageway 28 ensures that contaminants which are drawn away from the skin and into the vacuum passageway are immediately taken up by the contaminant absorber and thus immediately "immobilized" so that the movements of the contaminants during the measurement or treatment are minimized. Because the contaminants are electrically conductive, they may cause electrical disturbances as they are being carried away from the skin—the movements of the contaminants take place in an electric field—and it is important, therefore, that the movements be limited as far as possible. As is readily appreciated, the contaminant absorber 18 should therefore be positioned as close to the opening gap 28A of the vacuum passageway 28 as possible and preferably extend down into the vacuum passageway to a point close to the opening gap 28A or even through the opening gap down to the vicinity of the tip 24A of the sealing edge. However, when viewed from a production point of view, the position illustrated in FIGS. 1 and 2 is more advantageous.

Both the absorber disk 31 and the cover disk 32 have a central aperture of approximately the same diameter as the neck 27 of the sealing member. Together with the aperture region 32A of the relatively rigid cover disk 32, the bead 27A of the neck 27 forms a snap-lock connector which retains the contaminant absorber 18 on the sealing member 17 and at the same time the neck 27 centres the contaminant absorber on the sealing member.

Sealing member 17 is made of an electrically insulating material. It therefore functions as an electrical insulation between, on the one hand, the contaminant absorber 18 and, on the other hand, the electrode element 16 or the circumferential interior surface 21B which defines the recess 21A of the sealing member 17 and which in use contacts the electrode element.

As is apparent from the drawings, there is also no possibility of moisture migrating under capillary action from the absorber 18 and along the interface between the electrode element shank 20 and the collar 26 or the neck 27 of the sealing element. Moisture can migrate through the absorber 18 as far as up to the hub portion 21 of the sealing element 17, but the hub portion 21 provides an electrical insulation between the absorber 18 and the electrode element 16 or the circumferential surface 21B, and the outer circumferential surfaces of the collar 26 and the neck 27 form anti-capillary or capillary-breaking surfaces by being exposed to the air over a substantial height so that they effectively prevent migration of moisture downwardly and upwardly from the absorber 18. This prevention of migration of moisture is enhanced by the material of the sealing element 17 being hydrophobic.

Thus, the electrode element 16 has both an electrical insulation and a capillary break or interruption with respect to the contaminant absorber 18 and the areas of the skin which in use come into electrically conducting contact with the contaminant absorber.

With the construction according to the invention the skin surface with which the electrode element 16 is conductively connected will be well-defined.

Because the evacuation of the vacuum chamber portion that is below the sealing element body 22 takes place very close to the sealing edge 24 or, in other words, precisely where any leakage of air from the surrounding atmosphere into the vacuum chamber V takes place, the air entering the vacuum chamber is prevented from penetrating between the skin area inwardly of the gap 28A and the "ceiling", that is the underside 22A of the body 22.

In this arrangement of the evacuation lies an important difference from known electrode devices in which the evacuation takes place at the "ceiling", that is, in a manner such that air leaking into the vacuum chamber can pass from the sealing lip along the skin to the "ceiling". In these devices the air will cause variations in the layer of sweat and electrolytic agents and will consequently cause variations of the conductivity parameters of the electrical connection between the skin and the electrode element. If the electrode device is used in an environment comprising electrostatic fields, the leaking air will also result in dipole variations which interfere with the signals picked up from the skin.

Accordingly, the invention ensures that the "electrical environment" inside the sealing edge 24 or at least inside the edge 22C of the body portion 22B (meaning over almost the entire skin area within the vacuum chamber V) will remain essentially constant throughout the measurement or treatment.

Moreover, the invention offers a possibility of providing in a simple manner a substantial enlargement of the skin area inside the sealing element with which the electrode element is in low-ohmic electrical connection, without increasing the diameter of the sealing element or adversely affecting the vacuum holding power while maintaining the constant "electrical environment".

In the illustrated embodiment, this can be accomplished for example, by shaping and arranging the underside 22A of the sealing element body 22 such that electrolytic gel applied to the skin contact surface of the electrode element will be spread under the influence of the reduced pressure in the vacuum chamber such that a continuous layer of gel will be formed on the skin beneath the body 22 or a well-defined portion of it. The body 22, or the delimited portion of it, can then advantageously be provided with a conductive coating which in use of the electrode device contacts the electrode element 16. A delimitation of a portion of the sealing element body beneath which a layer of gel is provided may be brought about by providing a discontinuity in the body, an annular ridge or the like.

Alternatively, the skin contact member 19 of the electrode element 16 may be enlarged and shaped like a cupola.

As already mentioned, the annular gap 28A or outer vacuum chamber compartment V1 provides the main or sole fluid flow connection between the inner vacuum chamber compartment V2 and the upper side of the body 22. This arrangement is not necessary, however, as long as a sufficient vacuum can constantly be maintained in the gap 28A. As a matter of fact, certain advantages can be obtained if there is additionally an evacuation at the central portion of the vacuum chamber.

On the other hand, there is an advantage in having that portion of the vacuum chamber V which is located inwardly of the gap 28A, that is, the inner vacuum chamber compartment V1, substantially hermetically isolated from the vacuum system except at the gap 28A. If in that case an occasional brief loss or substantial reduction of the vacuum above the sealing element should occur after the vacuum electrode device has been applied to the skin and the skin has been drawn up into engagement with the sealing element body 22, e.g. as indicated by a phantom line in FIG. 1, this loss or reduction of vacuum will not be sensed at the skin area beneath the sealing element body 22, and therefore the holding power will remain until the full vacuum has been restored.

Figure 4A:
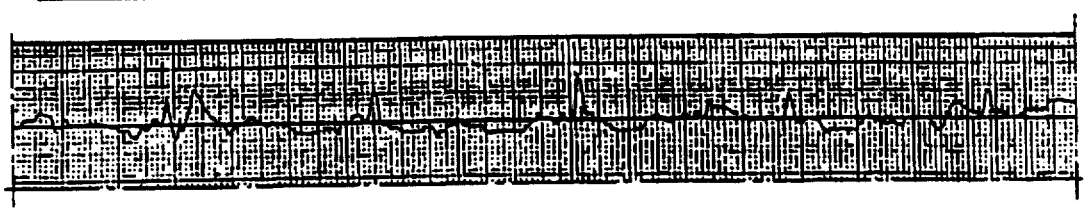
FIG. 4A and FIG. 4B show two ECGs.
Figure 4B:
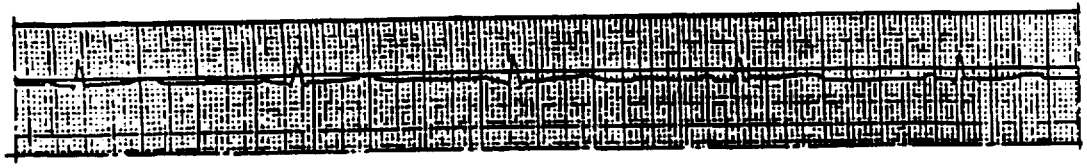

FIGS. 4A and 4B show two electrocardiograms. The ECG in FIG. 4A was recorded using an electrode device constructed as illustrated in the drawings except that the opening of the vacuum passageway into the vacuum chamber was not situated near the sealing edge of the sealing lip but near the upper horizontal or flat portion of the sealing element body. The ECG in FIG. 4B was recorded using the illustrated electrode devices under the same conditions.

Depending on the properties of the skin area to which the electrode device is applied, it may take a shorter or longer time for the skin to become drawn up into sealing engagement with the free edge 22C of the body portion 22B. If the skin is loose or very elastic or both, and free from hair, the sealing engagement may be brought about very rapidly. On the other hand, if the skin is tight or hairy, it may take rather a long time before an effective sealing has been brought about. If air should leak under the sealing lip 23 before the skin is in sealing engagement with the edge 22C, the picked up signal may be spurious.

Figure 5:
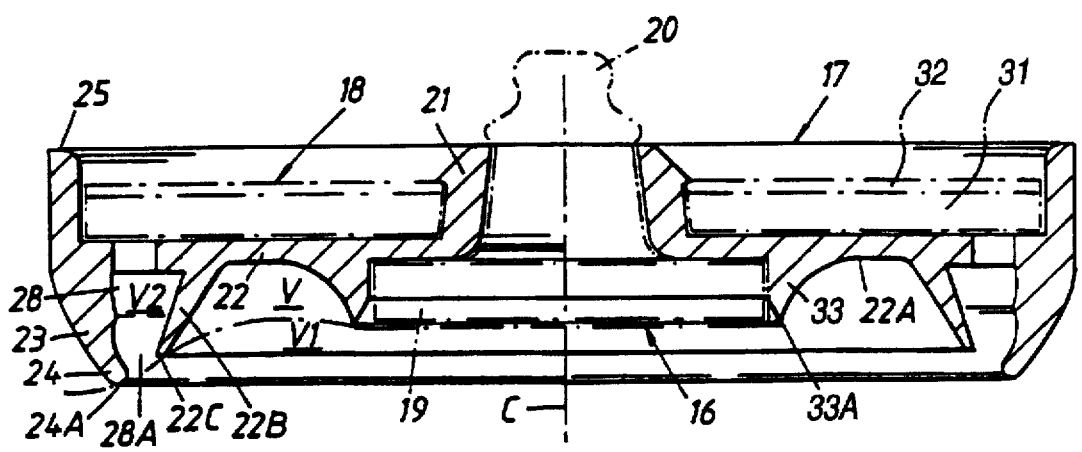
FIG. 5 is a sectional view similar to FIG. 2 of a modified embodiment of the sealing element.
Figure 6:
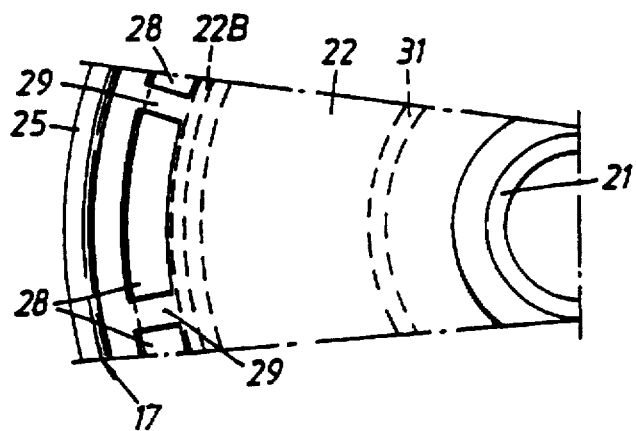
FIG. 6 is a fractional plan view of the sealing element of FIG. 5.
Figure 5A:
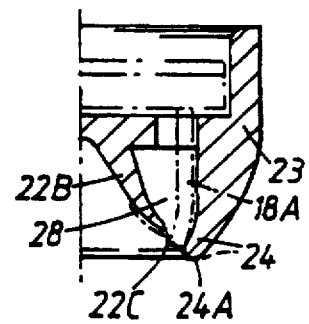
FIG. 5A is a fractional view of the sealing member of FIG. 5 with the sealing member held to the skin under action of vacuum.

These problems are avoided with the embodiment of the sealing element shown in FIGS. 5, 5A and 6, in which the same reference numerals as in FIGS. 1 and 2 are used to designate parts which are common or substantially common to the two embodiments.

In the embodiment of FIGS. 5, 5A and 6, the downwardly extending portion 22B of the sealing element 17 forms an inner annular sealing lip which is somewhat elastic so that its lower portion can be flexed outwardly toward the sealing lip 23 as shown in FIG. 5A. The flexibility may be brought about in different ways, such as by making the lower section relatively thin and undulating circumferentially or by slitting it axially.

Nearer to the centre of the sealing element 17, an annular collar or rib 33 is provided which terminates in a pointed tip 33A. This rib 31 surrounds a circular space which accommodates the plate-like skin contact member 19 of the electrode element 16. The tip 31A projects slightly, e.g. by a few tenths of one millimeter, past the level of the underside of the skin contact portion 19.

When the sealing element 17 is applied to the skin of the patient, the skin area subjected to the reduced pressure will be drawn upwardly into the vacuum chamber V. Almost directly after the reduced pressure has been applied, the skin will engage the sealing edge 22C of the sealing member portion or inner sealing lip 22B as is indicated by a phantom line to the right in FIG. 5 so that the compartment V1 of the vacuum chamber inside the sealing member portion 22B will be isolated from the compartment V2 outside it and thus from the vacuum passageway 28. Continued evacuation of the inner compartment V2 of the vacuum chamber V is still possible, however, because air may be drawn out beneath the edge 22C. Such continued evacuation is facilitated by the sealing element portion 22B being flexible so that it can yield outwardly, at least locally, to allow air to pass out of the vacuum chamber.

As the reduced pressure continues to act, the skin is drawn further upward. The skin will also be tightened around the sealing edge 24 of the sealing lip 23 and tend to be drawn outwardly into the vacuum passageway 28 indicated by a phantom line in FIG. 5A.

A suitable position of the sealing element portion or inner sealing lip 22B is that which is shown in FIG. 5 in which the edge 22C thereof is positioned slightly inwardly of, and slightly higher than, the sealing edge tip 24A. The distance separating the edge 22C from the sealing edge tip 24A is not critical but should be very small (e.g. a few tenths of one millimeter), because it is advantageous to have the line of engagement of the edge 22C with the skin spaced as far as possible from the electrode element 16. With a short radial distance it is also easier for the skin to become tightened around the sealing edge 24. The sealing member portion 22B, or at least the lower section of it, should therefore be movable outwardly by the force applied to it by the skin as indicated in FIG. 5A, even until it engages the sealing lip 23.

Moreover, it is within the scope of the invention to provide inwardly of the sealing element portion 22B, and preferably concentrically with it, one or more additional similar elements.

As soon as the electrode device is applied to the skin and the skin is subjected to the reduced pressure in the vacuum chamber V, the skin will be engaged by the skin contact member 19 of the electrode member 16 and by the tip 33A of the rib 33. This engagement will contribute to establishing a stable electrical environment for the electrode element 16.

Naturally, it is not necessary that the sealing element 17 is a separate, readily replaceable item as in the illustrated embodiment. Instead, it may form part of the electrode holder or head 11. Moreover, the sealing element need not necessarily be combined with a contaminant absorber.

The applicability of the invention is not restricted to electrode devices in which the contaminants are carried away exclusively with the aid of flowing air.

In an embodiment, not shown in the drawings, the contaminants are carried away by means of a moisture absorber which is mounted in moisture-transmitting relation to the lower or outer portion of the sealing lip, preferably the sealing edge thereof, and ensures that moisture at the annular zone adjacent to the sealing edge is directly carried away from that zone.

In this embodiment the removal of the moisture by means of a moisture absorber is combined with the removal of moisture by means of flowing air as in the illustrated embodiment. For example, the embodiment illustrated in the drawing may be modified to include a contaminant absorber portion (which may be a separate component or an extension of the absorber 18) positioned in the passageway 28 and reaching down to the sealing edge tip 24A or to a level very close to the sealing edge tip 24A. Such an absorber portion is indicated in phantom lines at 18A in FIG. 5A.

As in the embodiment illustrated in the drawings, the moisture absorber may be made of, or include, a superabsorbent material. It may be integrated in the sealing lip and, if desired, made as a single piece together with the sealing lip, but it may also be a separate component which is suitably combined with the sealing lip. The absorber may be arranged in such a manner that the absorbent material directly engages the skin and itself defines the zone from which moisture is to be carried away. Alternatively, the moisture may be transported from this zone to the absorber body through short passageways or pores in a portion of the sealing element made of a different material so that capillary forces can assist in the removal of the moisture from the skin to the absorber body.

Various changes and modifications to the presently preferred embodiments will be apparent to those skilled in the art. Such changes and modifications may be made without departing from the spirit and scope of the present invention and without diminishing its attendant advantages. Therefore, the appended claims are intended to cover such changes and modifications.

What is claimed is:

1. A sealing element for a vacuum electrode device, the sealing element comprising:

a vacuum cup defining a vacuum chamber adapted to accommodate a skin-engaging portion of an electrode element therein and communicating with a vacuum passageway through which a vacuum can be applied to the vacuum chamber, the vacuum cup having a skin-engageable outer sealing edge disposed around an opening to said vacuum chamber; and a narrow annular gap between the vacuum chamber and the outer sealing edge for conducting fluid away from the vacuum chamber towards the vacuum passageway, said gap being delimited outwardly by the outer sealing edge.

2. A sealing element according to claim 1, wherein the vacuum cup further includes:

an annular outer sealing lip which has an annular free end forming said outer sealing edge; and a body having a generally disk-shaped portion concentrically positioned within said vacuum chamber, the body defining an annular inner sealing lip which includes a skin-engageable inner sealing edge spaced from said outer sealing edge to form said narrow annular gap, said body subdividing the vacuum chamber into a central inner vacuum chamber compartment bounded by the annular inner sealing lip and disk-shaped portion and an outer annular vacuum chamber compartment between the annular inner sealing lip and the annular outer sealing lip into which the vacuum passageway opens.

3. A sealing element according to claim 2, wherein the inner sealing edge is spaced radially inwardly from the outer sealing lip and lies in a generally common plane therewith.

4. A sealing element according to claim 2, wherein the inner sealing lip is flexible.

5. A sealing element according to claim 2, wherein the disk-shaped portion of the body extends generally transversely from a central axis of the sealing element, and wherein a peripheral portion of the body carries the inner sealing lip which is positioned at the vacuum passageway.

6. A sealing element according to claim 2, wherein the disk-shaped body portion of the body has a central recess for accommodating a skin-engaging portion of an electrode element and wherein the body has an annular skin-engaging rib disposed concentrically around said recess and concentrically inwardly of the inner sealing lip, said rib being adapted to project into the inner vacuum chamber compartment slightly past the skin-engaging portion of the electrode member.

7. A sealing element according to claim 2, further comprising:

a moisture absorber which is disposed in fluid flow communication with the outer vacuum chamber compartment.

8. A sealing element according to claim 7, wherein the moisture absorber extends into the outer vacuum chamber compartment.

9. A sealing element according to claim 2, wherein said means for conducting fluid towards the vacuum passageway comprises capillary passages in the outer sealing lip.

10. A sealing element according to claim 1, wherein said means for conducting fluid towards the vacuum passageway comprises a moisture absorber element in the annular gap.

11. A vacuum electrode device comprising:

an electrode head having means for connecting it to a source of vacuum and to an apparatus for processing electric signals, and a sealing element comprising:

a vacuum cup defining a vacuum chamber adapted to accommodate a skin-engaging portion of an electrode element therein and communicating with a vacuum passageway through which a vacuum can be applied to the vacuum chamber, the vacuum cup having a skin-engageable outer sealing edge disposed around an opening to said vacuum chamber; and a narrow annular gap between the vacuum chamber and the outer sealing edge for conducting fluid away from the vacuum chamber towards the vacuum passageway, said gap being delimited outwardly by the outer sealing edge.

12. A vacuum electrode device according to claim 11, wherein the vacuum cup further includes:

an annular outer sealing lip which has an annular free end forming said outer sealing edge; and a body having a generally disk-shaped portion concentrically positioned within said vacuum chamber, the body having an annular inner sealing lip which includes a skin-engageable inner sealing edge spaced from said outer sealing edge to form said narrow annular gap, said body subdividing the vacuum chamber into a central inner vacuum chamber compartment bounded by the inner annular sealing lip and the disk shaped portion and an outer annular vacuum chamber compartment between the inner annular sealing lip and the outer annular sealing lip into which the vacuum passageway opens.

13. A vacuum electrode device according to claim 12, wherein the inner sealing edge is spaced radially inwardly from the outer sealing lip and lies in a generally common plane therewith.

14. A vacuum electrode device according to claim 12, wherein the inner sealing lip is flexible.

15. A vacuum electrode device according to claim 12, wherein the disk-shaped portion of the body extends generally transversely from a central axis of the sealing element, and wherein a peripheral portion of the body carries the inner sealing lip which is positioned at the vacuum passageway.

16. A vacuum electrode device according to claim 12, wherein the disk-shaped portion of the body has a central recess for accommodating a skin-engaging portion of an electrode element and wherein the body has an annular skin-engaging rib disposed concentrically around said recess and concentrically inwardly of the inner sealing lip, said rib being adapted to project into the inner vacuum chamber compartment slightly past the skin-engaging portion of the electrode member.

17. A vacuum electrode device according to claim 12, further comprising:

a moisture absorber which is disposed in fluid flow communication with the outer vacuum chamber compartment.

18. A vacuum electrode device according to claim 17, wherein the moisture absorber extends into the outer vacuum chamber compartment.

19. A vacuum electrode device according to claim 12, wherein said means for conducting fluid towards the vacuum passageway comprises capillary passages in the outer sealing lip.

20. A vacuum elelectrode device according to claim 11, wherein said means for conducting fluid towards the vacuum passageway comprises a moisture absorber element in the annular gap.

* * * * *